US009662484B2

(12) United States Patent
Woolley et al.

(10) Patent No.: US 9,662,484 B2
(45) Date of Patent: May 30, 2017

(54) NEUROSURGICAL DEVICE AND METHOD

(71) Applicant: RENISHAW PLC, Wotton-under-Edge (GB)

(72) Inventors: Maxwell Woolley, Bristol (GB); Trefor Lewis, Olveston (GB)

(73) Assignee: RENISHAW PLC, Wotton-Under-Edge (GB)

( * ) Notice: Subject to any disclaimer, the term of this patent is extended or adjusted under 35 U.S.C. 154(b) by 0 days.

(21) Appl. No.: 14/431,133

(22) PCT Filed: Oct. 2, 2013

(86) PCT No.: PCT/GB2013/052559
§ 371 (c)(1),
(2) Date: Mar. 25, 2015

(87) PCT Pub. No.: WO2014/053826
PCT Pub. Date: Apr. 10, 2014

(65) Prior Publication Data
US 2015/0273202 A1 Oct. 1, 2015

(30) Foreign Application Priority Data
Oct. 2, 2012 (GB) .................................. 1217606.1

(51) Int. Cl.
A61M 39/02 (2006.01)

(52) U.S. Cl.
CPC . A61M 39/0247 (2013.01); A61M 2039/0261 (2013.01); A61M 2039/0264 (2013.01);
(Continued)

(58) Field of Classification Search
CPC ...... A61M 39/0247; A61M 2039/0261; A61M 2039/025; A61M 2210/0687
See application file for complete search history.

(56) References Cited

U.S. PATENT DOCUMENTS

| 4,013,074 A | 3/1977 | Siposs |
| 4,511,355 A | 4/1985 | Franetzki et al. |

(Continued)

FOREIGN PATENT DOCUMENTS

| CN | 2684843 Y | 3/2005 |
| CN | 101384286 A | 3/2009 |

(Continued)

OTHER PUBLICATIONS

Jul. 31, 2015 Office Action issued in U.S. Appl. No. 13/575,759.
(Continued)

Primary Examiner — Aarti B Berdichevsky
(74) Attorney, Agent, or Firm — Oliff PLC

(57) ABSTRACT

A skull mountable, implantable percutaneous fluid delivery device is described for use in delivering fluids to target sites in the brain. The device includes a subcutaneous base portion including one or more ports for supplying fluid to one or more implanted catheter devices. A percutaneous portion of the device includes an extracorporeal surface, the one or more ports of the subcutaneous base portion being accessible from the extracorporeal surface of the percutaneous portion. The subcutaneous base portion is at least partially insertable into a complementary recess formed in a bone and includes one or more anchoring features including at least one radially protruding wing for directly anchoring the subcutaneous base portion to the bone.

16 Claims, 4 Drawing Sheets

(52) U.S. Cl.
CPC .............. *A61M 2039/0276* (2013.01); *A61M 2039/0282* (2013.01); *A61M 2210/0687* (2013.01)

(56) References Cited

U.S. PATENT DOCUMENTS

| | | | |
|---|---|---|---|
| 4,578,063 A | 3/1986 | Inman et al. | |
| 4,634,422 A | 1/1987 | Kantrowitz et al. | |
| 4,692,147 A | 9/1987 | Duggan | |
| 4,695,273 A | 9/1987 | Brown | |
| 4,705,464 A | 11/1987 | Arimond | |
| 4,790,826 A | 12/1988 | Elftman | |
| 4,897,081 A | 1/1990 | Poirier et al. | |
| 4,903,707 A | 2/1990 | Knute et al. | |
| 5,098,397 A | 3/1992 | Svensson et al. | |
| 5,120,313 A | 6/1992 | Elftman | |
| 5,171,216 A | 12/1992 | Dasse et al. | |
| 5,221,474 A | 6/1993 | Yokono et al. | |
| 5,352,207 A | 10/1994 | Nussbaum | |
| 5,549,581 A | 8/1996 | Lurie et al. | |
| 5,752,930 A | 5/1998 | Rise et al. | |
| 5,782,645 A | 7/1998 | Stobie et al. | |
| 5,833,655 A | 11/1998 | Freed et al. | |
| 5,836,935 A | 11/1998 | Ashton et al. | |
| 5,906,596 A | 5/1999 | Tallarida | |
| 5,916,200 A * | 6/1999 | Eppley | A61M 25/02 604/174 |
| 5,954,687 A | 9/1999 | Baudino | |
| 5,990,382 A * | 11/1999 | Fox | A61B 10/00 623/16.11 |
| 6,018,094 A * | 1/2000 | Fox | A61B 10/00 606/191 |
| 6,044,304 A | 3/2000 | Baudino | |
| 6,134,477 A * | 10/2000 | Knuteson | A61M 25/02 607/115 |
| 6,454,774 B1 * | 9/2002 | Fleckenstein | A61B 5/031 600/451 |
| 6,471,689 B1 | 10/2002 | Joseph et al. | |
| 6,607,504 B2 | 8/2003 | Haarala et al. | |
| 6,609,020 B2 | 8/2003 | Gill | |
| 6,758,841 B2 | 7/2004 | Haarala et al. | |
| 6,840,919 B1 * | 1/2005 | Håkansson | A61M 39/0247 439/39 |
| 6,852,106 B2 | 2/2005 | Watson et al. | |
| 7,331,940 B2 * | 2/2008 | Sommerich | A61M 39/0247 604/175 |
| 7,833,204 B2 | 11/2010 | Picha | |
| 8,323,270 B2 | 12/2012 | Shachar et al. | |
| 8,827,987 B2 | 9/2014 | Fielder et al. | |
| 8,974,422 B2 | 3/2015 | Gill et al. | |
| 2003/0004520 A1 | 1/2003 | Haarala et al. | |
| 2003/0023208 A1 | 1/2003 | Osypka et al. | |
| 2003/0120215 A1 | 6/2003 | Bousquet | |
| 2003/0130577 A1 | 7/2003 | Purdy et al. | |
| 2003/0171711 A1 | 9/2003 | Rohr et al. | |
| 2003/0171738 A1 | 9/2003 | Konieczynski et al. | |
| 2004/0034367 A1 | 2/2004 | Malinowski | |
| 2004/0243064 A1 | 12/2004 | Sommerich | |
| 2004/0249361 A1 | 12/2004 | Denoth et al. | |
| 2004/0260361 A1 | 12/2004 | Gibson | |
| 2004/0267238 A1 | 12/2004 | Haarala et al. | |
| 2005/0075624 A1 | 4/2005 | Miesel | |
| 2005/0203486 A1 * | 9/2005 | Sommerich | A61M 39/0247 604/891.1 |
| 2005/0245887 A1 | 11/2005 | Olsen et al. | |
| 2005/0283203 A1 | 12/2005 | Flaherty et al. | |
| 2007/0255262 A1 | 11/2007 | Haase | |
| 2008/0287910 A1 | 11/2008 | Picha | |
| 2009/0030373 A1 | 1/2009 | Gill | |
| 2009/0082758 A1 | 3/2009 | Gill et al. | |
| 2009/0227989 A1 | 9/2009 | Burke et al. | |
| 2010/0042070 A1 | 2/2010 | Gill et al. | |
| 2010/0069892 A1 | 3/2010 | Steinbach et al. | |
| 2010/0145162 A1 | 6/2010 | Devauchelle et al. | |
| 2012/0310182 A1 * | 12/2012 | Fielder | A61M 5/14276 604/264 |
| 2014/0343500 A1 * | 11/2014 | Fielder | A61M 5/14276 604/175 |
| 2014/0371679 A1 * | 12/2014 | Woolley | A61M 39/0247 604/173 |

FOREIGN PATENT DOCUMENTS

| | | |
|---|---|---|
| CN | 101400386 A | 4/2009 |
| CN | 101537224 A | 9/2009 |
| CN | 101541356 A | 9/2009 |
| DE | 20115120 U1 | 3/2002 |
| DE | 10143820 A1 | 3/2003 |
| EP | 0266243 A1 | 5/1988 |
| EP | 0992257 A1 | 4/2000 |
| EP | 1426074 A1 | 6/2004 |
| EP | 1 481 697 A1 | 12/2004 |
| EP | 1576975 A1 | 9/2005 |
| EP | 1704891 B1 | 6/2011 |
| FR | 2690625 A1 | 11/1993 |
| FR | 2750054 A1 | 12/1997 |
| GB | 2389791 A | 12/2003 |
| GB | 2459101 A | 10/2009 |
| JP | S48-5290 A | 1/1973 |
| JP | S62-240069 A | 10/1987 |
| JP | H02-168968 A | 6/1990 |
| JP | H03-126438 A | 5/1991 |
| JP | H03-286776 A | 12/1991 |
| JP | H05-42220 A | 2/1993 |
| JP | H08-141088 A | 6/1996 |
| JP | H11-504231 A | 4/1999 |
| JP | 2001-505115 A | 4/2001 |
| JP | 2001-509063 A | 7/2001 |
| JP | 2004-000495 A | 1/2004 |
| JP | 2006-520656 A | 9/2006 |
| JP | 2006-263470 A | 10/2006 |
| JP | 2006-525827 A | 11/2006 |
| JP | 2009-526589 A | 7/2009 |
| WO | 8907467 A1 | 8/1989 |
| WO | 96/29953 A1 | 10/1996 |
| WO | 9749438 A1 | 12/1997 |
| WO | 98/31417 A2 | 7/1998 |
| WO | 9934754 A1 | 7/1999 |
| WO | 0112158 A1 | 2/2001 |
| WO | 03/077785 A1 | 9/2003 |
| WO | 03077784 A1 | 9/2003 |
| WO | 2004/084768 A2 | 10/2004 |
| WO | 2004105839 A1 | 12/2004 |
| WO | 2007093778 A1 | 8/2007 |
| WO | 2007104953 A1 | 9/2007 |
| WO | 2007104961 A1 | 9/2007 |
| WO | 2008/062173 A1 | 5/2008 |
| WO | 2009047494 A1 | 4/2009 |
| WO | 2009094389 A1 | 7/2009 |
| WO | 2009/103758 A2 | 8/2009 |
| WO | 2009096851 A1 | 8/2009 |
| WO | 2009128959 A1 | 10/2009 |
| WO | 2011098769 A1 | 8/2011 |

OTHER PUBLICATIONS

Jul. 1, 2015 Office Action issed in Chinese Patent Application No. 201210084254.7.
Dec. 11, 2015 Search Report issued in European Application No. 15 18 1867.
Oct. 9, 2014 Office Action issued in Japanese Application No. 2012-552463.
Nov. 14, 2014 Office Action issued in Japanese Application No. 2012-552462.
Feb. 25, 2015 Office Action issued in Chinese Application No. 201180009002.1.
Jun. 30, 2011 Written Opinion of International Search Report issued in PCT/GB2011/000183.
Jun. 30, 2011 Written Opinion of International Search Report issued in PCT/GB2011/000182.

(56) References Cited

OTHER PUBLICATIONS

U.S. Appl. No. 13/575,759, filed Jul. 27, 2012 in the name of Fielder et al.
May 21, 2010 Search Report issued in Patent Application No. GB1002370.3.
"Linear Incision Technique—Procedure and clinical results". BAHA Clinical Review.
N.K.O. & Hoofd-Halsheelkunde, "Bone Anchored Hearing Aids (B.A.H.A.)". http://www.nko.uza.be/prof/baha/index.html. Oct. 11, 2008. 5 pages.
Borenstein, Jeffrey T. "Medicine by Micromachine". IEEE Spectrum. Nov. 2009. Int. pp. 35-39.
Bovo, R. "Simplified technique without skin flap for the bone-anchored hearing aid (BAHA) implant". ACTA Otorhinolaryngologica Italica 2008. 28, pp. 252-255. Ferrara, Italy.
Jul. 25, 2013 Office Action issued in Chinese Patent Application No. 201180009336.9.
Aug. 16, 2013 Office Action issued in Chinese Patent Application No. 201180009002.1.
Mar. 3, 2014 Office Action issued in Chinese Patent Application No. 201180009336.9.
Jun. 23, 2014 Office Action issued in Chinese Patent Application No. 201180009002.1.
Lundgren et al. "Soft-Tissue-Anchored Percutaneous Device for Long-Term Intracorporeal Access." Journal of Investigative Surgery. vol. 2, pp. 17-27.1989.
Fricova et al. "The Implantable Intravenous Ports". Bolest. 2006. pp. 165-172.
Nyman et al. "Soft-Tissue-Anchored Transcutaneous Port for Long-Term Percutaneous Transhepatic Biliary Drainage". CardioVascular and Interventional Radiology. vol. 28, pp. 53-59. 2005.
Berntorp et al. "Experience with a new percutaneous port system, Percuseal, for intravenous injection in patients with haemophilia, von Willebrand disease and severe alpha.sub.1-antitrypsin deficiency". Haemophilia. vol. 9, pp. 173-178. 2003.
Germano et al. "Surgical Techniques for Stereotactic Implant of Deep Brain Stimulators". Seminars in Neurosurgery. vol. 12, No. 2, pp. 213-223. 2001.
"Lead Kit for Deep Brain Stimulation". Medtronic Manual, pp. 9-56. 2002.
May 6, 2013 Chinese Office Action issued in Application No. 201210084254.7.
Jul. 6, 2012 Office Action issued in Japanese Patent Application No. 2009-537691.
Mar. 25, 2014 Office Action issued in Chinese Application No. 201210084254.7.
Sep. 20, 2013 Office Action issued in Japanese Application No. 2009-537691.
Dec. 12, 2014 Office Action issued in Canadian Application No. 2,670,164.
Nov. 15, 2014 Office Action issued in Chinese Application No. 201210084254.7.
Oct. 18, 2013 Office Action issued in U.S. Appl. No. 13/575,769.
Feb. 24, 2014 Office Action issued in U.S. Appl. No. 13/575,769.
U.S. Appl. No. 14/581,549, filed Dec. 23, 2014 in the name of Gill et al.
May 9, 2014 Office Action issued in U.S. Appl. No. 12/312,584.
Dec. 18, 2013 Office Action issued in U.S. Appl. No. 12/312,584.
Aug. 10, 2011 Office Action issued in U.S. Appl. No. 12/312,584.
Dec. 6, 2010 Office Action issued in U.S. Appl. No. 12/312,584.
Apr. 4, 2008 International Search Report issued in International Patent Application No. PCT/GB2007/004438.
Jun. 30, 2011 International Search Report issued in International Patent Application No. PCT/GB2011/000183.
Jun. 30, 2011 International Search Report issued in International Patent Application No. PCT/GB2011/000182.
Jan. 31, 2014 International Search Report issued in International Patent Application No. PCT/GB2013/052559.
Dec. 31, 2012 Search Report issued in GB Patent Application No. 1217606.01.
Jan. 31, 2014 Written Opinion of International Search Report issued in International Patent Application No. PCT/GB2013/052559.
U.S. Appl. No. 14/445,626, filed Jul. 29, 2014 in the name of Fielder et al.
Apr. 4, 2008 Written Opinion of International Search Report Issued in PCT/GB2007/004438.
May 17, 2016 Office Action issued in European Application No. 11 706 900.5.
May 13, 2016 Office Action issued in Chinese Application No. 201210084254.7.
Jul. 20, 2016 Office Action issued in Chinese Patent Application No. 201380051627.3.
Nov. 4, 2016 Office Action Issued in U.S. Appl. No. 14/445,626.
Apr. 26, 2016 Office Action Issued in U.S. Appl. No. 14/445,626.
May 2, 2016 Office Action issued in Japanese Application No. 2015-166782.
Jun. 17, 2016 Office Action issued in U.S. Appl. No. 13/575,759.
Nov. 4, 2016 Office Action issued in Chinese Patent Application No. 201410772721.4.
Mar. 14, 2017 Office Action Issued in U.S. Appl. No. 13/575,759.
Mar. 14, 2017 Office Action issued in U.S. Appl. No. 14/581,549.

\* cited by examiner

NEUROSURGICAL DEVICE AND METHOD

The present invention relates to drug delivery apparatus and in particular to improved neurological drug delivery apparatus comprising a skull mountable percutaneous fluid delivery device.

The drug treatment of a number of neuro-degenerative disorders, hereditary neurological disorders, brain tumours and other diseases of the nervous system are compromised by the presence of the blood brain barrier which prevents the transfer of drugs from the vascular system or cerebrospinal fluid into the brain substance. Examples of drugs which do not adequately cross the blood brain barrier include protein molecules such as neurotrophins, monoclonal antibodies, viral particles for delivery of gene therapy, as well as a number of cytotoxic drugs for the treatment of tumours. It has been described previously how such drugs can be delivered to the brain by direct infusion into the parenchyma via one or more indwelling catheter. For example, a guide tube and catheter system is described in U.S. Pat. No. 6,609,020. A catheter with a small external diameter that can be precisely positioned in the brain is described in WO2003/077785. Percutaneous access ports have also been described in WO2008/062173 and WO2011/098769.

The percutaneous fluid delivery devices described in WO2011/098769 comprise a subcutaneous base portion that can be inserted into a recess formed in bone. One or more features on the base portion act to grip the bone and thereby secure the device to the subject. Although such a device performs well, it has been found that detachment of the device may occur when implanted in certain animal models. The present invention thus relates to an improvement to the percutaneous fluid delivery device of WO2011/098769.

According to a first aspect of the invention, an implantable percutaneous fluid delivery device is provided that comprises;
  a subcutaneous base portion comprising one or more ports for supplying fluid to one or more implanted catheter devices, and
  a percutaneous portion comprising an extracorporeal surface, the one or more ports of the subcutaneous base portion being accessible from the extracorporeal surface of the percutaneous portion,
  wherein the subcutaneous base portion is at least partially insertable into a complementary recess formed in a bone and comprises one or more anchoring features for directly anchoring the subcutaneous base portion to the bone,
  characterised in that the one or more anchoring features comprise at least one radially protruding wing.

The present invention thus relates to an implantable percutaneous fluid delivery device or port unit for use in delivering fluid, such as therapeutic agents, to selected targets within the body. The implantable percutaneous fluid delivery device has one or more outlets or ports that are separately connectable to one or more implanted catheter devices. The implantable percutaneous fluid delivery device is particularly suited for use in delivering therapeutic agents to targets within the brain using one or more associated implanted intraparenchymal catheter devices.

The implantable percutaneous fluid delivery device comprises a subcutaneous base portion comprising one or more ports for supplying fluid to one or more implanted catheter devices. The term subcutaneous as used herein is intended to define a location below the outer surface of the skin. As described below, the subcutaneous base portion is preferably implantable below all of the skin. A percutaneous portion is also provided as part of the device that extends from the subcutaneous base portion and comprises an extracorporeal surface. As would be understood by those skilled in the art, when implanted a percutaneous device crosses the skin to provide a connection between the inside and outside of the body. The one or more ports of the subcutaneous base portion are accessible from the extracorporeal surface of the percutaneous portion; in other words, the extracorporeal surface (i.e. a surface accessible from outside of the body) provides fluidic access to the one or more outlet ports of the subcutaneous base portion of the device. It should be noted that the subcutaneous base portion and percutaneous portion may be formed together or may be formed as separate components that are attached together before use.

The subcutaneous base portion of the device of the first aspect of the present invention has one or more anchoring features for directly anchoring the subcutaneous base portion to the bone. In particular, the one or more anchoring features comprise at least one radially protruding wing. The provision of such a radially protruding wing has been found to stabilise the device and allow more secure attachment to bone. This is especially advantageous when implanting the device in thin skull bones that are covered in muscle. The device is thus preferably used for non-human subjects, such as primates.

Any number of radially protruding wings may be provided. Advantageously, the device comprises a plurality of radially protruding wings. Preferably, three or more radially protruding wings are provided. In a preferred embodiment, three radially protruding wings are provided; these may be spaced apart from one another by approximately 120 degrees. Alternatively, three radially protruding wings may be provided that are spaced apart by approximately 90 degrees.

The device may comprise a subcutaneous base portion having a central hub for press fit attachment to a hole formed in the skull. The central hub may include any of the features described in WO2011/098769. In addition, said at least one radially protruding wing preferably extends from the central hub. The central hub may be approximately cylindrical. The central hub may have a radius. Each wing preferably extends radially from the hub by a distance greater than half the radius of the hub. Each wing may radially extend from the hub by a distance that is greater than the radius of the hub. Each wing may radially extend from the hub by at least 0.5 mm, more preferably by at least 1 mm, more preferably by at least 2 mm, more preferably by at least 3 mm or more preferably by at least 4 mm.

The radially protruding wings may be of any suitable shape. Advantageously, each radially protruding wing has a rounded distal end or tip. Some or all of the radially protruding wings may comprise an aperture for receiving a bone screw. The wing may then be secured to the skull by a screw. This may aid attachment to the subject prior to the osseointegration of the device. Each wing may curve upwards (i.e. away from the subject) as it extends radially. The distal end of each wing may sit on the surface of the bone. For example, the distal end of each wing may sit on the surface of the bone adjacent the aperture in the bone that is formed to receive the central hub.

Each radially protruding wing may comprise one or more apertures to promote osseointegration. Each radially protruding wing preferably comprises a plurality of apertures extending through the wing to promote osseointegration. For example, each radially protruding wing may comprise a substrate (e.g. a sheet of metal) with one or more holes formed therein. Alternatively, each radially protruding wing may be formed from a mesh (e.g. a "chicken wire" type structure) or from a porous material. Such structures allow bone to grow through the apertures to anchor the device to the bone.

Advantageously, at least part of the subcutaneous base portion comprises a coating or surface texture to promote osseintegration. The coating or surface texture may be applied to the at least one radially protruding wing and/or to any central hub.

When implanted, at least part (and preferably most) of the subcutaneous base portion is located below the outer surface of a bone. The device preferably includes a feature or features that allow the depth of insertion of the device into an appropriate recess formed in a bone to be predefined. Advantageously, the subcutaneous base portion comprises a protruding lip or step(s) for engaging the outer surface of a bone around the periphery of a recess formed in that bone. Such a lip thus sits on the outermost bone surface when inserted and, as well as setting the depth of insertion, also allows the device to be implanted in a hole that passes all the way through a bone.

The device may be made using any suitable manufacturing technique. For example, by machining, selective laser sintering or 3D printing.

The invention also extends to a device as described above in combination with at least one neurosurgical catheter.

The invention also extends to a device as described above in combination with a fluid connector for attachment to the extracorporeal surface to provide fluid access to said one or more ports.

The invention also extends to a method of neurosurgery. The method may include the steps of forming a recess in the skull of a subject and implanting a device as described above in said recess. The surgically formed recess may be shaped to receive the device. The implantation technique described in WO2011/098769 is preferably used.

As explained above, the present invention is an improvement to the device that is described in WO2011/098769. The whole contents of WO2011/098769 are thus incorporated herein by reference. The device of the present invention may thus further comprise any feature described in WO2011/098769.

The invention will now be described, by way of example only, with reference to the accompanying drawings in which.

Figure 1:
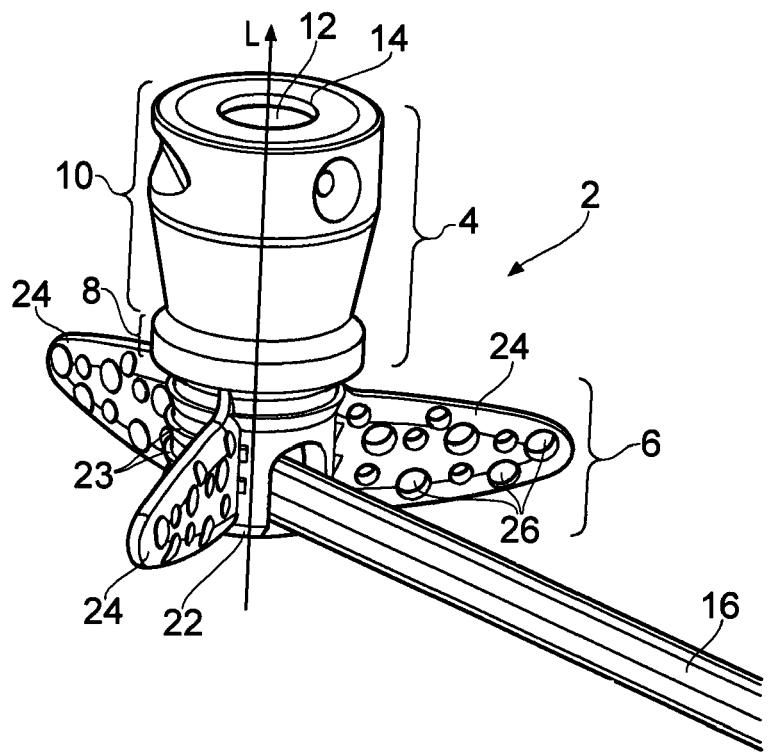
FIG. 1 shows a percutaneous fluid delivery device of the present invention.
Figure 2:
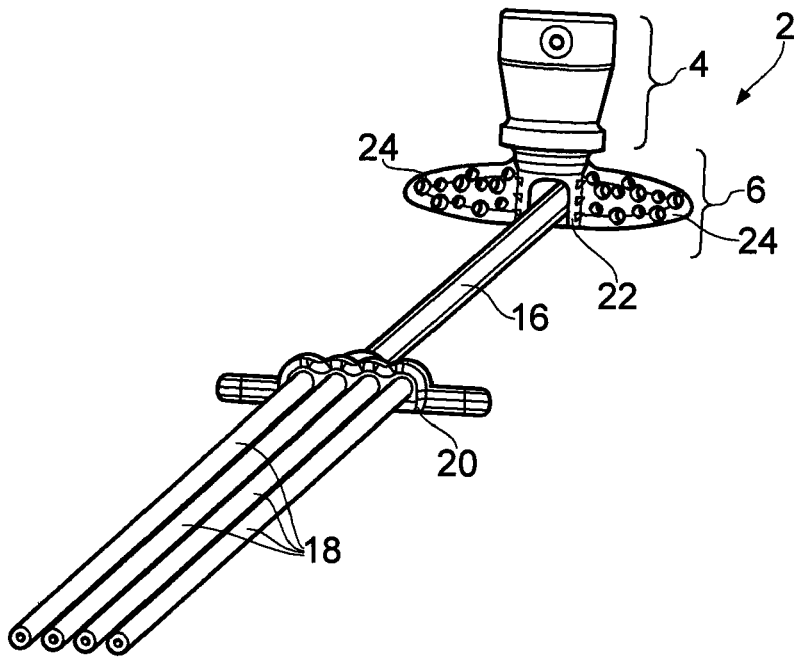
FIG. 2 is an alternative view of the device of FIG. 1.

Referring to FIGS. 1 and 2, an implantable percutaneous fluid delivery device 2 of the present invention is illustrated.

The device 2 comprises a percutaneous portion 4 and a subcutaneous base portion 6. The percutaneous portion 4 includes a transcutaneous region 8 that is roughened to promote skin adhesion and an extracorporeal surface 10. The side walls of the extracorporeal surface 10 are smooth to allow cleaning. A septum seal 12 is accessible via a top surface 14. The septum seal 12 provides fluidic access to ports provided in the subcutaneous base portion 6 that are also connected to a four-lumen supply tube 16. The supply tube 16 is further connected to four intracranial fluid delivery catheters 18 via a fluid hub 20. The device 2 may be formed as a single piece or from multiple parts and may include any of the internal or external configurations that are described in detail in WO2011/098769.

The present invention relates to the improved subcutaneous base portion 6. The base portion 6 comprises a central hub 22 that comprises broaching fins or ribs 23 for engaging and gripping a complementary hole formed in the bone of a subject. The central hub 22 also includes three radially protruding wings 24. In other words, the device has a longitudinal axis L that is typically arranged to be approximately perpendicular to the surface of the bone, when implanted. The wings 24 extend outwardly from the central hub 22 in directions perpendicular to the longitudinal axis L (i.e. they extend radially). The bone recess that is formed in the subject prior to implantation of the device will thus include a central aperture for receiving the central hub 22 and three radially extending slots corresponding to the size and spacing of the radially protruding wings 24. Each of the radially protruding wings 24 also comprises multiple apertures 26. These apertures 26 help promote osseointegration (i.e. bone can grow through the apertures thereby securing the device in place). Although three equidistantly spaced wings are shown, it should be note that a different number of wings could be provided and the radial spacing could be altered as required.

The implantable percutaneous fluid delivery device may be used as part of the drug delivery apparatus described in WO2011/098769. For example, the percutaneous fluid delivery device may be connected to one or more implantable intracranial catheters.

Figure 3:
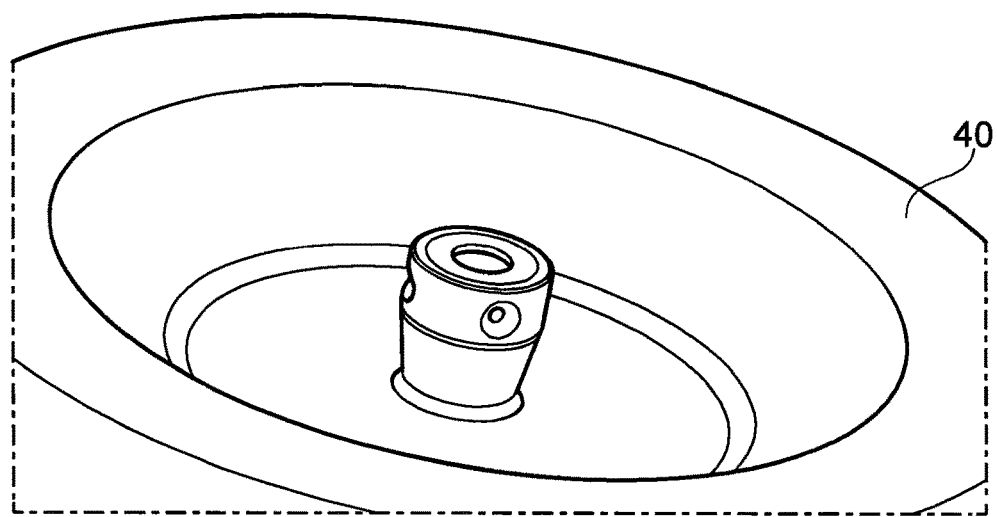
FIG. 3 illustrates the device when implanted as viewed from the exterior of the subject.

Referring to FIG. 3, there is provided an illustration of how the device will sit in the skin (i.e. dermis 40) after the graft has taken. It should be noted that the sunken area is where the hypodermal layers have been removed and the dermal layer has adhered to the periosteum.

Figure 4:
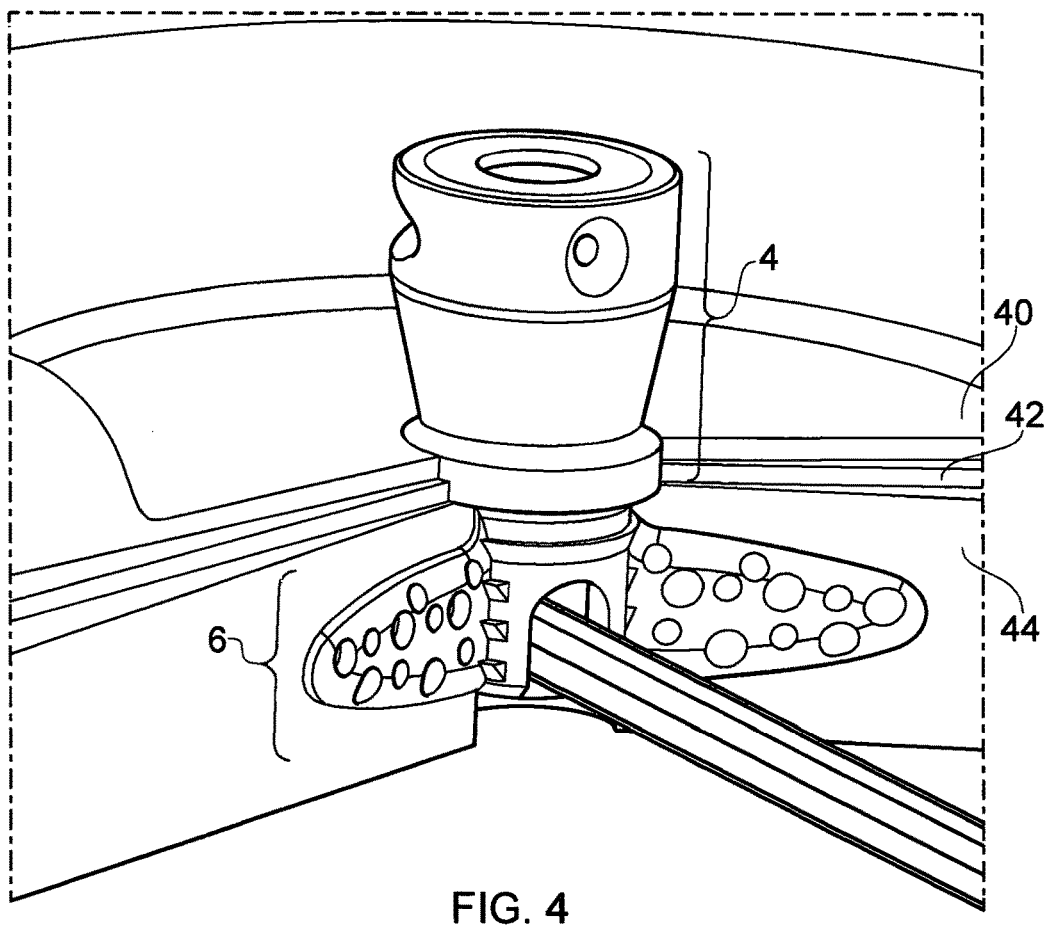
FIG. 4 is a cut-away view of the device when implanted.

FIG. 4 shows a sectioned view of the device implanted into the model's skull. The dermis 40, periosteum 42 and bone 44 are shown. Again, it can be noted how the bone is shown following a period of healing. During surgical implantation, burred and/or drilled bone fragments are preferably packed back in around the implanted device to maximise rate of recovery.

Figure 5:
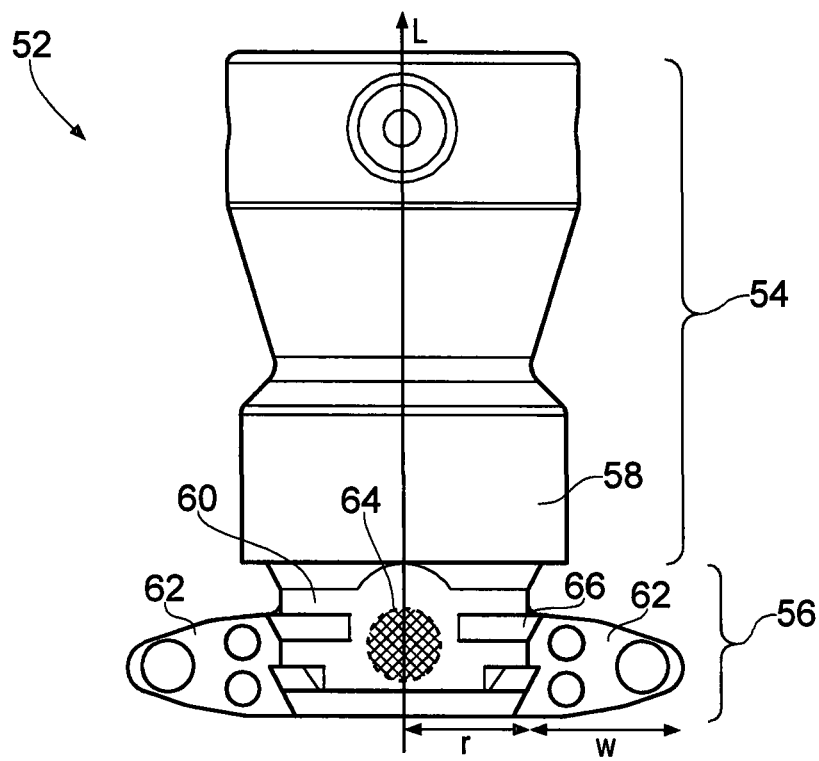
FIG. 5 shows a first variant of the device of FIG. 1.

FIG. 5 shows an implantable percutaneous fluid delivery device 52 that has a similar structure to the device described above with reference to FIGS. 1 to 4. The device 52 comprises a percutaneous portion 54 and a subcutaneous base portion 56. The percutaneous portion 54 is similar to the percutaneous portion 4 described above, although the transcutaneous region 58 is longer than that described above to reduce dermal growth over the device.

The subcutaneous base portion 56 comprises a central hub 60 and three protruding wings 62 (noting that only two of the wings 62 are illustrated in the cross-sectional vie of FIG. 5). The central hub 60 is approximately cylindrical and has a central longitudinal axis L and a radius r. The wings 62 protrude radially from the hub 60 and have a radial length w. As explained above, it is preferred the distance w that the wings extend from the hub is greater than half the radius r of the hub. In this example, the wings 62 extend from the hub 60 by a distance w that is slightly larger than the radius r. In this example, the three wings 62 are spaced 90° apart from each other around the hub, with a supply tube exiting the hub 60 at the position 64 shown as hatched outline in FIG. 5. Although small broaching fins 66 are also provided to aid press-fit attachment to the hole formed in the skull, the three wings 62 provide stabilisation of the device within the bone.

Figure 6:
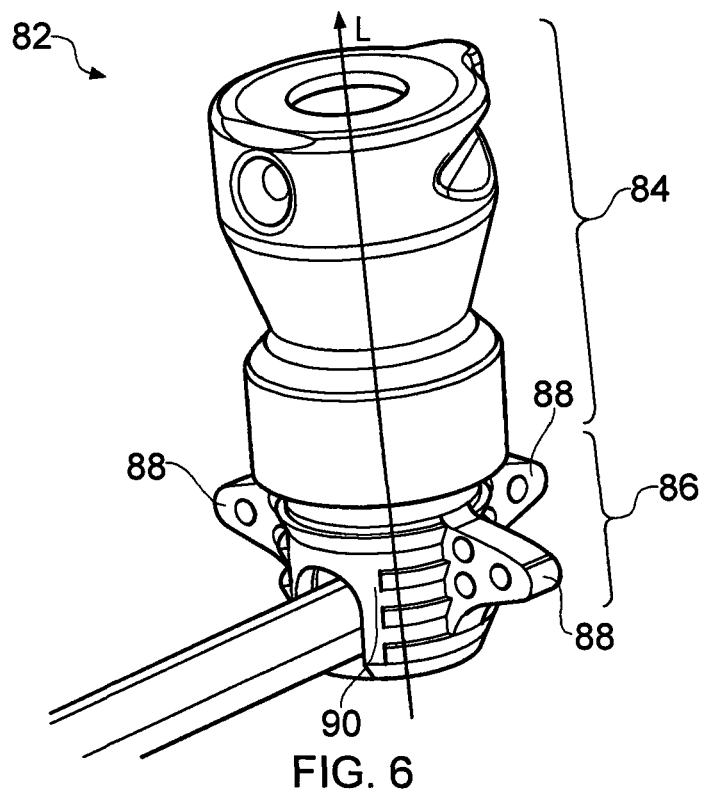
FIG. 6 shows a further variant of the device of FIG. 1.

FIG. 6 shows an implantable percutaneous fluid delivery device 82 that has a similar structure to the devices described above with reference to FIGS. 1 to 5. The device 82 also includes a percutaneous portion 84 and a subcutaneous base portion 86. The device 82 has a central hub 90 and three protruding wings 88. Each wing 88 lies in a plane that includes the longitudinal axis L. The wings 88 do not extend the full length of the subcutaneous base portion 86. Instead, the lower ends of the wings 88 are set back from the distal (lower) end of the subcutaneous base portion 86. Similarly, the upper ends of the wings 88 are set back from the proximal (upper) end of the subcutaneous base portion 86.

Although FIG. 6 is for illustration purposes only and is not drawn to scale, the radial tips of the wings 88 are located approximately 5.5 mm from the longitudinal axis L. The lower and upper ends of the wings 88 are also set back approximately 2 mm and 1 mm respectively from the lower and upper ends of the subcutaneous base portion 86. It should, of course, be noted that these dimensions are provided for the purpose of illustrating the invention and should not be seen as limiting the size of devices that may be provided in accordance with the present invention. Providing wings as illustrated in FIG. 6 has been found to be advantageous as it allows the device 82 to be implanted in areas of the skull with larger curvatures; i.e. it ensures the wings do not penetrate the skin or dig deeper into the skull when the skull curves away from the hub.

Figure 7:
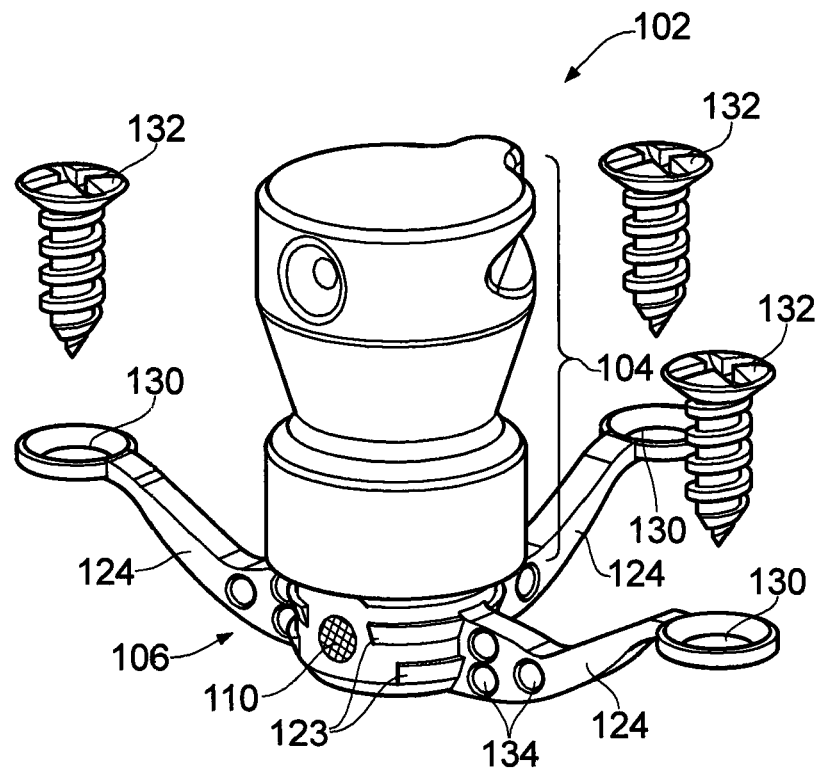
FIG. 7 shows a screw anchored variant of the device of FIG. 1.
Figure 8:
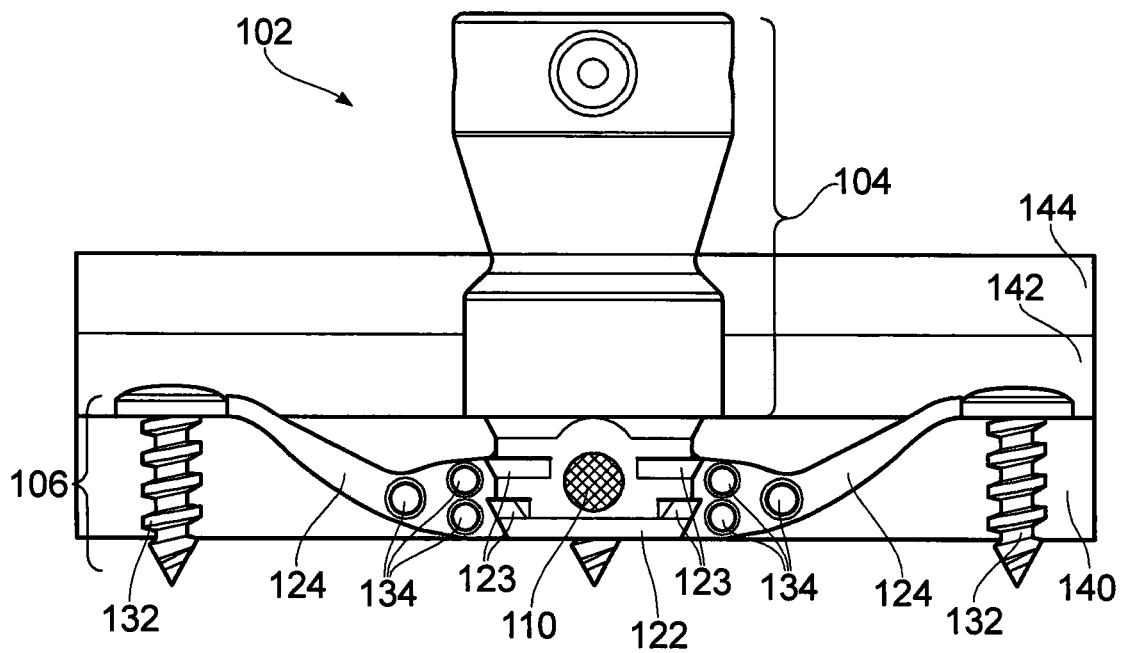
FIG. 8 shows the device of FIG. 7 when screwed in place.

Referring to FIGS. 7 and 8, a further implantable percutaneous fluid delivery device 102 is illustrated.

The device 102 includes a percutaneous portion 104 and a subcutaneous base portion 106. The percutaneous portion 104 is similar to those described above with reference to FIGS. 1 to 6. The subcutaneous base portion 106 comprises a central hub 122 with fins or ribs 123 for engagement with a bone recess. Three wings 124 protrude from the central hub 122. The wings 124 are radially spaced apart by 90° and a supply tube exit 110 (shown in hatched outline in FIGS. 7 and 8) is provided radially opposite one of the wings 124. Each wing 124 has a proximal end attached to the central hub 122. The distal end of each wing 124 includes an aperture 130 for securing the wing 124 to the bone of the subject with a bone screw 132. A plurality of holes 134 are provided near the proximal end of each wing 124 to promote osseointegration.

FIG. 7 shows the device 102 and bone screws 132 prior to use, whilst FIG. 8 illustrates the device 102 and bone screws 132 after implantation in a subject. The bone 140, temporal facia 142 and dermis 144 are also illustrated in FIG. 8. It can be seen that the central hub 122 and proximal ends of each wing 124 lie within a recess formed with the bone 140. Each wing 124 is shaped to curve upwardly towards the surface of the bone layer and to have a distal end (comprising the aperture 130) that sits on the surface of the bone. This allows attachment of the device to the bone 140 using bone screws 132, thereby immediately securing the device to the subject. Osseointegration can then occur on a slower time scale to further secure the device in place, but the screws 132 allow the device to be used immediately after implantation and stabilise the device whilst osseointegration takes place.

The invention claimed is:

1. An implantable percutaneous fluid delivery device comprising:

a subcutaneous base portion comprising one or more ports for supplying fluid to one or more implanted catheter devices; and a percutaneous portion comprising an extracorporeal surface, the one or more ports of the subcutaneous base portion being accessible from the extracorporeal surface of the percutaneous portion, wherein the subcutaneous base portion is at least partially insertable into a complementary recess formed in a bone and comprises one or more anchoring features for directly anchoring the subcutaneous base portion to the bone, the one or more anchoring features comprise at least one radially protruding wing extending from the subcutaneous base portion, the at least one radially protruding wing has a proximal end adjacent the subcutaneous base portion, the proximal end of the at least one radially protruding wing being configured to lie within the complementary recess formed within the bone, and the at least one radially protruding win has a lower surface that curves upwardly towards an outer surface of the bone as it extends outwardly from the subcutaneous base portion.

2. A device according to claim 1, wherein the one more anchoring features comprise a plurality of radially of protruding wings.

3. A device according to claim 1, wherein the one or more anchoring features comprise three or more radially protruding wings.

4. A device according to claim 1, wherein the one or more anchoring features comprise three radially protruding wings.

5. A device according to claim 4, wherein the radially protruding wings are spaced apart from one another by approximately 120 degrees.

6. A device according to claim 1, wherein the subcutaneous base portion comprises a central hub for press fit attachment to a hole formed in the bone, the at least one radially protruding wing extending from the central hub.

7. A device according to claim 1, wherein the at least one radially protruding wing has a rounded distal end.

8. A device according to claim 1, wherein the at least one radially protruding wing comprises one or more apertures to promote osseointegration.

9. A device according to claim 8, wherein the at least one radially protruding wing comprises a plurality of apertures extending through the wing to promote osseointegration.

10. A device according to claim 1, wherein at least part of the subcutaneous base portion comprises a coating or surface texture to promote osseointegration.

11. A device according to claim 1, further comprising a lip to set a depth of insertion of the device into a bone recess.

12. A device according to claim 1, wherein the at least one radially protruding wing has a distal end that is configured to sit on a surface of the bone.

13. A device according to claim 1, wherein the at least one radially protruding wing has a distal end comprising at least one aperture for securing the at least one radially protruding wing to the bone with a bone screw.

14. Neurosurigcal apparatus comprising a device according to claim 1 and at least one neurosurgical catheter.

15. Neurosurigcal apparatus comprising a device according to claim 1 and a fluid connector for attachment to the extracorporeal surface to provide fluid access to said one or more ports.

16. A method of neurosurgery, comprising the steps of forming a recess in a skull of a subject and implanting a device according to claim 1 in the recess, the recess being shaped to receive the device.

* * * * *